(12) United States Patent
Altarac et al.

(10) Patent No.: US 8,114,092 B2
(45) Date of Patent: Feb. 14, 2012

(54) INSERTER FOR A SPINAL IMPLANT

(75) Inventors: Moti Altarac, Irvine, CA (US); Stanley Kyle Hayes, Mission Viejo, CA (US); Tyler Jay Haskins, Oceanside, CA (US)

(73) Assignee: Exactech, Inc., Gainesville, FL (US)

( * ) Notice: Subject to any disclaimer, the term of this patent is extended or adjusted under 35 U.S.C. 154(b) by 919 days.

(21) Appl. No.: 12/156,857

(22) Filed: Jun. 4, 2008

(65) Prior Publication Data
US 2008/0306488 A1 Dec. 11, 2008

Related U.S. Application Data

(60) Provisional application No. 60/933,538, filed on Jun. 7, 2007.

(51) Int. Cl.
*A61B 17/58* (2006.01)
*A61B 17/60* (2006.01)
*A61F 2/00* (2006.01)

(52) U.S. Cl. .......................................... 606/99; 606/914
(58) Field of Classification Search ................ 606/86 A, 606/99, 914; 623/17.11–17.16; 81/177.8, 81/177.9
See application file for complete search history.

(56) References Cited

U.S. PATENT DOCUMENTS

| | | | |
|---|---|---|---|
| 6,186,034 B1 * | 2/2001 | Lamons ........................ | 81/177.9 |
| 7,060,073 B2 | 6/2006 | Frey et al. | |
| 7,575,580 B2 * | 8/2009 | Lim et al. ........................ | 606/99 |
| 2004/0064136 A1 | 4/2004 | Papineau et al. | |
| 2005/0096745 A1 * | 5/2005 | Andre et al. ................ | 623/17.11 |
| 2005/0131408 A1 | 6/2005 | Sicvol et al. | |
| 2006/0084988 A1 | 4/2006 | Kim | |
| 2006/0235426 A1 | 10/2006 | Lim et al. | |
| 2007/0213737 A1 * | 9/2007 | Schermerhorn et al. ........ | 606/86 |
| 2008/0306489 A1 | 12/2008 | Altarac et al. | |
| 2008/0306557 A1 | 12/2008 | Altarac et al. | |
| 2010/0100138 A1 | 4/2010 | Reynolds et al. | |

FOREIGN PATENT DOCUMENTS

WO 2007035892 3/2007

OTHER PUBLICATIONS

Non-Final Office Action for U.S. Appl. No. 12/157,647 mailed on Sep. 15, 2010.
Final Office Action for U.S. Appl. No. 12/157,647 mailed on Mar. 22, 2010.
Non-Final Office Action for U.S. Appl. No. 12/215,497 mailed on Jul. 14, 2011.

* cited by examiner

*Primary Examiner* — Thomas C. Barrett
*Assistant Examiner* — Andrew Yang
(74) *Attorney, Agent, or Firm* — Meyertons, Hood, Kivlin, Kowert & Goetzel, P.C.; Eric B. Meyertons

(57) ABSTRACT

An inserter for implanting an intervertebral spacer into a spinal disc space is disclosed. The inserter comprises a jaw assembly connected to a shaft assembly that is connected to a handle assembly. The user operates the handle assembly to open and close the jaw assembly to thereby connect to and release from the intervertebral spacer. Furthermore, the handle assembly is operable to lock and unlock rotation of the jaw assembly while still connected thereto to permit angulation of the jaw assembly relative to the shaft assembly without losing hold of the intervertebral spacer.

20 Claims, 12 Drawing Sheets

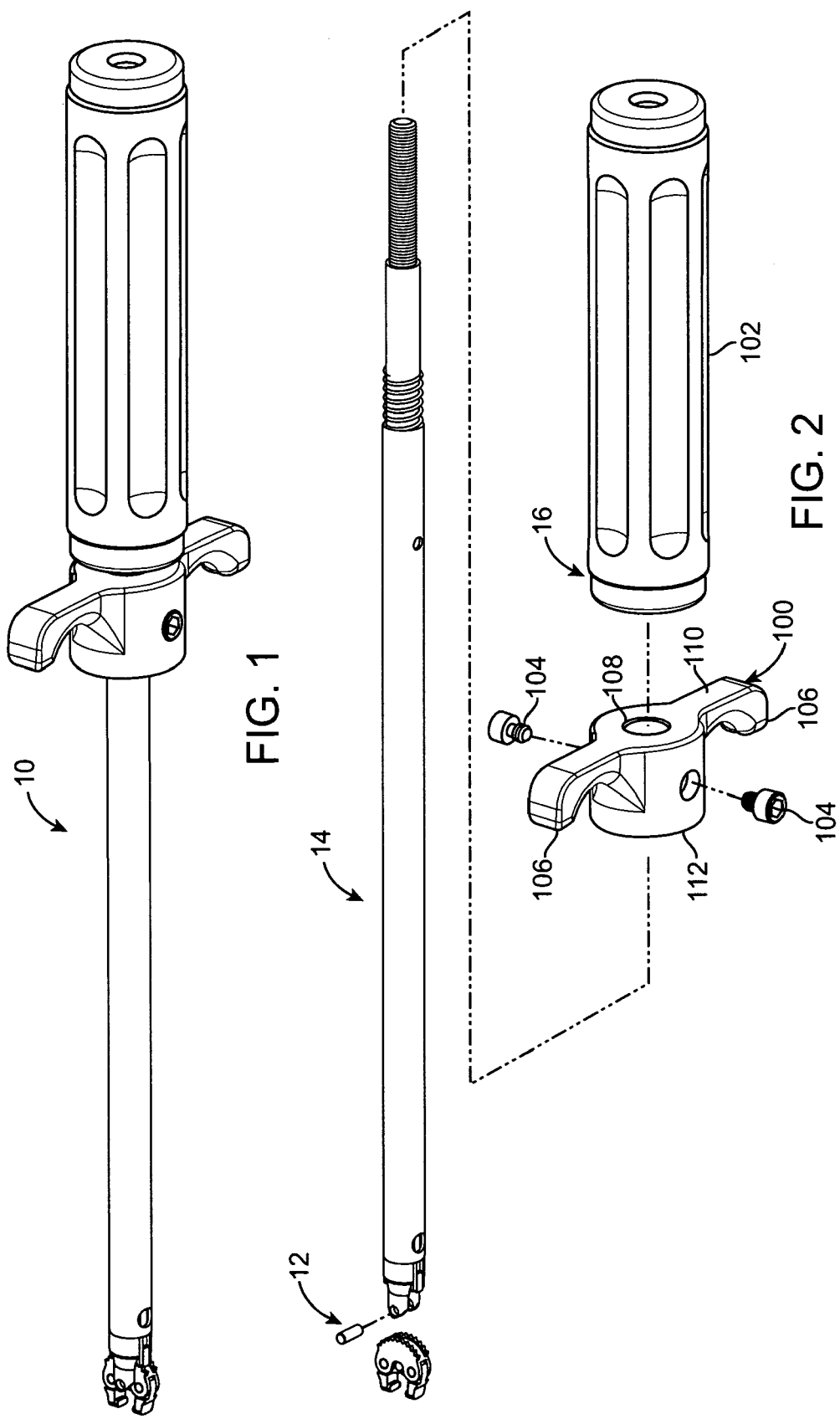

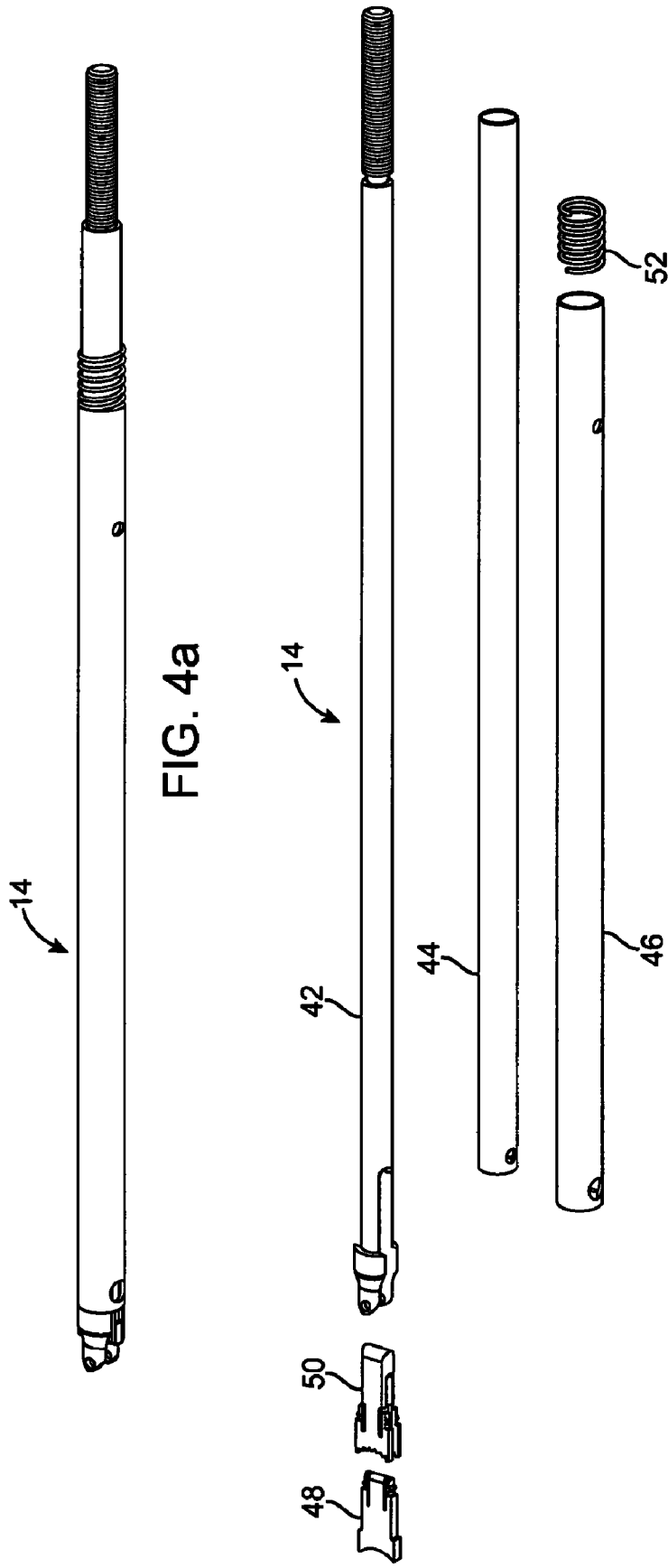

INSERTER FOR A SPINAL IMPLANT

CROSS-REFERENCE TO RELATED APPLICATIONS

This application claims priority to and the benefit of U.S. Provisional Patent Application Ser. No. 60/933,538 entitled "Inserter for intervertebral spacer" filed on Jun. 7, 2007 which is incorporated herein by reference in its entirety.

FIELD

The present invention generally relates to medical devices, and in particular, the present invention relates to a surgical instrument for introducing implants related to the spine.

BACKGROUND

Deterioration or dislocation of a spinal disc located between two adjacent vertebral bodies often results in the two adjacent vertebral bodies coming closer together. The reduced disc space height typically results in instability of the spine, decreased mobility and pain and discomfort for the patient. A common treatment is to surgically restore the proper disc space height to thereby alleviate the neurologic impact of the collapsed disc space. Typically, most surgical corrections of a disc space include at least a partial discectomy which is followed by restoration of normal disc space height and, in some instances, fusion of the adjacent vertebral bodies. Restoration of normal disc space height generally involves the implantation of a spacer and fusion typically involves inclusion of bone graft or bone graft substitute material into the intervertebral disc space to create bony fusion. Fusion rods may also be employed. Some implants further provide artificial dynamics to the spine. Such techniques for achieving interbody fusion or for providing artificial disc functions are well-known in the art.

One problem, among others, with inserting an implant, for example, is associated with patient anatomy. Inserting and positioning the implant in the space between adjacent vertebrae can be difficult or time consuming if the bony portions are spaced too close together, or if the adjacent tissue, nerves or vasculature impedes access to or placement of the implant in the space between the bony portions. Furthermore, maintenance of distraction of the space during insertion of the implant requires additional instruments in the operative space which can make the procedure more invasive and impede access and visibility during implant insertion and thereby make the procedure more difficult.

Another difficulty of implant insertion is related to the point of access to the damaged disc space which may be accomplished from several approaches to the spine with each approach having different associated difficulties. One approach is to gain access to the anterior portion of the spine through a patient's abdomen. For an anterior approach, extensive vessel retraction is often required and many vertebral levels are not readily accessible from this approach. Another approach is a posterior approach. This approach typically requires that both sides of the disc space on either side of the spinal cord be surgically exposed, which may require a substantial incision or multiple access locations, as well as extensive retraction of the spinal cord. Yet another approach is a postero-lateral approach to the disc space. The posterolateral approach is employed in a posterior lumbar interbody fusion (PLIF) or transforaminal lumber interbody fusion (TLIF) procedure which may be performed as an open technique which requires making a larger incision along the middle of the back. Through this incision, the surgeon then cuts away, or retracts, spinal muscles and tissue to access the vertebrae and disc space. The TLIF procedure may also be performed as a minimally invasive or as an extreme lateral interbody fusion (XLIF) procedure that involves a retroperitoneal transpoas approach to the lumbar spine as an alternative to "open" fusion surgery. In the minimally invasive procedure, the surgeon employs much smaller incisions, avoids disrupting major muscles and tissues in the back and reduces the amount of muscle and tissue that is cut or retracted. As a result, blood loss is dramatically reduced and these minimally invasive benefits also lead to shorter hospital stays and quicker patient recovery times. The aforementioned and various other difficulties associated with the point of access to the damaged disc space and the need to navigate an implant insertion instrument through the point of access further place demands on the implant insertion instrument design.

Therefore, there remains a need for improved insertion instruments, implants and techniques for use in any one or more types of approaches to the disc space that facilitate and provide for effective insertion while saving time, minimizing the degree of invasiveness for the patient and complementing surgeon skill demands.

SUMMARY

According to one aspect of the invention, an inserter for implanting a spinal implant is disclosed. The inserter includes a jaw assembly configured to connect to the spinal implant. The inserter includes a shaft assembly connected to the jaw assembly. The jaw assembly is configured to angulate with respect to the shaft assembly. The inserter includes a handle assembly connected to the shaft assembly such that the handle assembly is operable by a user to (1) close and open the jaw assembly to thereby respectively connect the spinal implant to the jaw assembly and release the spinal implant from the jaw assembly; and (2) lock and unlock movement of the jaw assembly to permit angulation of the jaw assembly and thereby permit angulation of a connected spinal implant when angulation is unlocked; such angulation being relative to the shaft assembly while the spinal implant remains connected to the jaw assembly. The proximal end of the jaw assembly includes shaft engaging features and the distal end of the shaft assembly includes jaw assembly engaging features. The inserter is configured such that angulation of the jaw assembly is locked by engaging the jaw assembly engaging features of the shaft assembly to the shaft engaging features of the jaw assembly such that angulation of the jaw assembly is unlocked by disengaging the jaw assembly engaging features of the shaft assembly from the shaft engaging features of the jaw assembly. The shaft assembly is configured to move relative to the jaw assembly wherein movement of the shaft assembly closer to the jaw assembly engages the jaw assembly engaging features of the shaft assembly to the shaft engaging features of the jaw assembly and movement of the shaft assembly apart from the jaw assembly disengages the jaw assembly engaging features of the shaft assembly from the shaft engaging features of the jaw assembly. The handle assembly is configured to effect movement of the shaft assembly relative to the jaw assembly. In one variation, the shaft engaging features and the jaw assembly engaging features are teeth.

According to another aspect of the present invention, an inserter for implanting a spinal implant is disclosed. The inserter includes a jaw configured to releasably connect to the spinal implant, a shaft connected to the jaw such that the jaw is movable with respect to the shaft and a handle connected to the shaft. The inserter is configured such that the angle of the spinal implant with respect to the shaft can be repeatedly changed and locked in position while the spinal implant is connected to the inserter. The inserter is operable to lock and unlock the attached spinal implant to permit angulation without disconnecting the inserter from the spinal implant.

According to another aspect of the present invention, an inserter for implanting a spinal implant is disclosed. The inserter includes a jaw assembly configured to connect to the spinal implant. The jaw assembly includes a jaw having a first jaw piece and a second jaw piece and a jaw link connected to the first and second jaw pieces such that the first and second jaw pieces are movable with respect to the jaw link. The inserter further includes a shaft assembly connected to the jaw assembly. The shaft assembly includes an inner shaft connected to the jaw assembly, and an outer shaft having a central bore and located over the inner shaft. The shaft assembly further includes an angulation lock connected to the distal end of outer shaft. The inserter further includes a handle assembly connected to the shaft assembly. The handle assembly includes a handle connected to the inner shaft. The handle is operable to close and open the jaw to thereby attach and release the spinal implant to and from the jaw. The handle assembly further includes a knob connected to the outer shaft and movable with respect to the handle to engage and disengage the angulation lock to and from the jaw assembly so as to disable and enable angulation of the jaw assembly and hence of the attached spinal implant with respect to the shaft assembly. The handle is operable to close and open the jaw by moving the inner shaft proximally and distally with respect to the jaw. In another variation, the inserter further includes a middle shaft having a bore. The middle shaft is located over the inner shaft and inside the outer shaft. A pusher configured to engage the jaw link is provided and connected to the distal end of the middle shaft. The inserter is configured such that distal motion of the pusher by action of the handle engages the pusher to the jaw link to lock the jaw link relative to the shaft assembly.

According to another aspect of the present invention, a method for implanting a spinal implant in a patient is provided. The method includes the steps of creating an incision in a patient and providing a spinal implant. An inserter that has a handle at the proximal end and a distal end that is configured to releasably connect to the spinal implant such that the spinal implant is capable of angulation with respect to the inserter is provided. The spinal implant is connected to the inserter at the distal end of the inserter. The spinal implant is locked relative to the inserter such that the spinal implant is not capable of angulation with respect to the inserter. The spinal implant is inserted into a location inside the patient. The spinal implant is unlocked relative to the inserter such that the spinal implant is capable of angulation with respect to the inserter while the spinal implant remains connected to the inserter. The spinal implant is angulated relative to the inserter while the implant is connected to the inserter. The spinal implant is disconnecting from the inserter and removed from the patient. The spinal implant is locked relative to the inserter such that the spinal implant is not capable of angulation with respect to the inserter after angulating the spinal implant relative to the inserter. The inserter with the spinal implant connected is moved to a second location inside the patient.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 1 illustrates a perspective view of an inserter according to the present invention.

FIG. 2 illustrates an exploded perspective view of the inserter of FIG. 1 according to the present invention.

FIG. 4a illustrates a perspective view of a shaft assembly of the inserter according to the present invention.

FIG. 4b illustrates an exploded perspective view of the shaft assembly of the inserter according to the present invention.

DETAILED DESCRIPTION

Figure 3A:
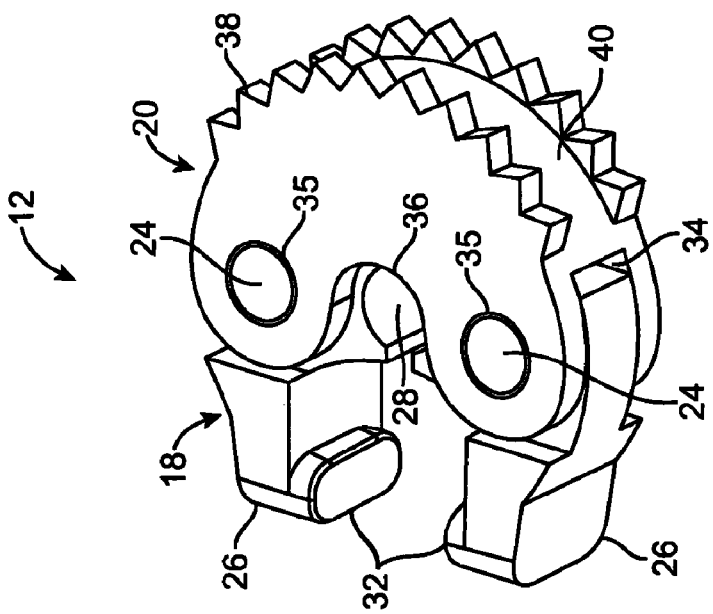
FIG. 3a illustrates a perspective view of a jaw assembly of the inserter according to the present invention.

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinal segrnent" may include a plurality of such spinal segments and reference to "the screw" includes reference to one or more screws and equivalents thereof known to those skilled in the art, and so forth.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention is described in the accompanying figures and text as understood by a person having ordinary skill in the field of spinal implants and related instrumentation.

Referring now to FIG. 1, there is shown a perspective view of an inserter 10 for inserting an intervertebral spacer into a disc space between two adjacent vertebral bodies. An exploded perspective view of the inserter instrument 10 is shown in FIG. 2. As seen in FIG. 2, the inserter 10 includes a jaw assembly 12, a shaft assembly 14 and a handle assembly 16.

Figure 3B:
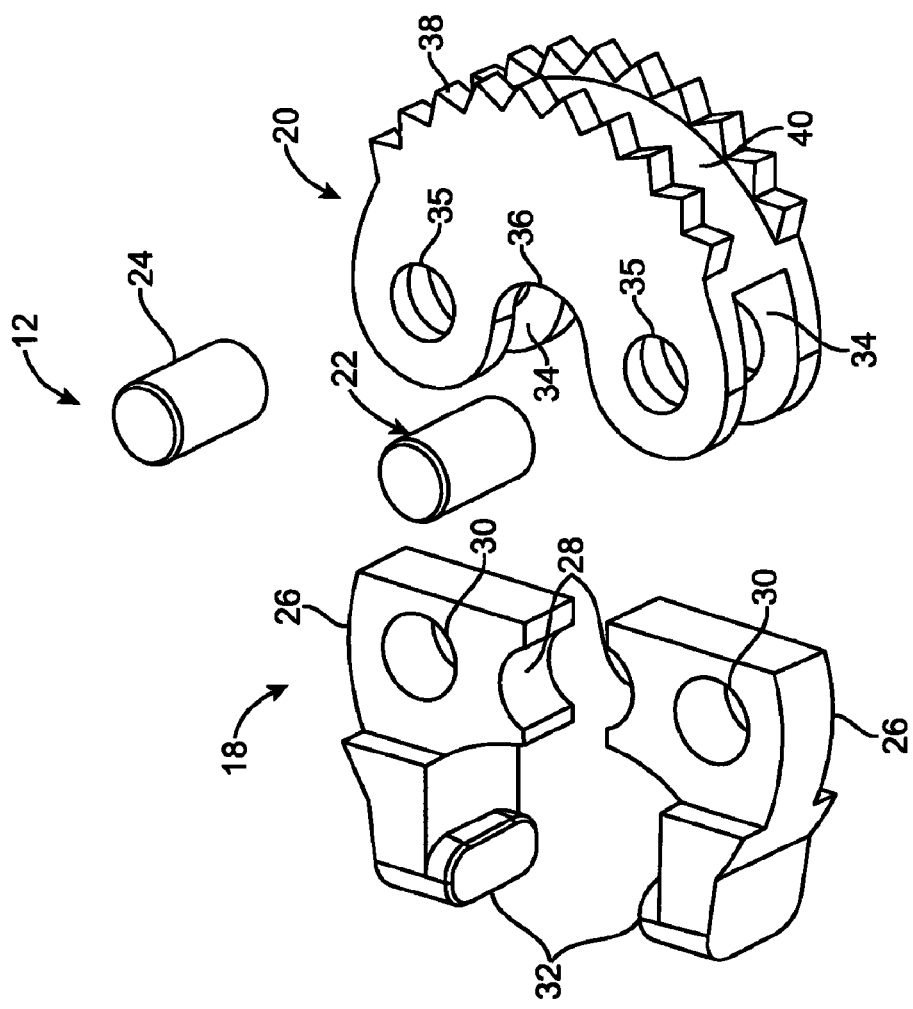
FIG. 3b illustrates an exploded perspective view of the jaw assembly of the inserter according to the present invention.

Turning now to FIGS. 3a and 3b, there are shown perspective and exploded perspective views, respectively, of the jaw assembly 12 according to the present invention. The jaw assembly 12 includes a jaw 18, a jaw link 20, a jaw pin 22, and two fasteners 24 (only one shown in FIG. 3b).

Still referencing FIGS. 3a and 3b, the jaw 18 includes two jaw pieces 26. Each jaw piece 26 includes a jaw pin receiving portion 28, a bore 30 for receiving fastener 24 and spacer engaging features 32. The spacer engaging features 32 are extending features configured to engage the interbody spacer (not shown). The features are projections configured to be inserted into complementarily shaped apertures in the interbody spacer.

Still referencing FIGS. 3a and 3b, the jaw link 20 includes jaw receiving portions 34 configured to receive each of the jaw pieces 26 and to be fastened together via fasteners 24 inserted through holes 35 such that the jaw pieces 26 are capable of movement with respect to the jaw link 20. The jaw link 20 also includes a jaw pin receiving portion 36 configured to receive the jaw pin 22. At the other end, the jaw link 20 includes a plurality of teeth 38 and a pusher engaging surface 40. The jaw pieces 26 of the jaw 18 are inserted into the jaw receiving portions 34 of the jaw link 20. The jaw pin 22 is disposed within the jaw pin receiving portion 28 of each jaw piece 26 and within the jaw pin receiving portion 36 of the jaw link 20. Fasteners 24 are passed through holes 35 of the jaw link 20 and through bores 30 in the jaw pieces 26, thereby, connecting the jaw 18 and the jaw link 20.

Turning now to FIGS. 4a and 4b, there are shown perspective and exploded perspective views, respectively, of the shaft assembly 14 according to the present invention. The shaft assembly 14 includes an inner shaft 42, a middle shaft 44, an outer shaft 46, a pusher 48, an angulation lock 50, and a spring 52.

Figure 4C:
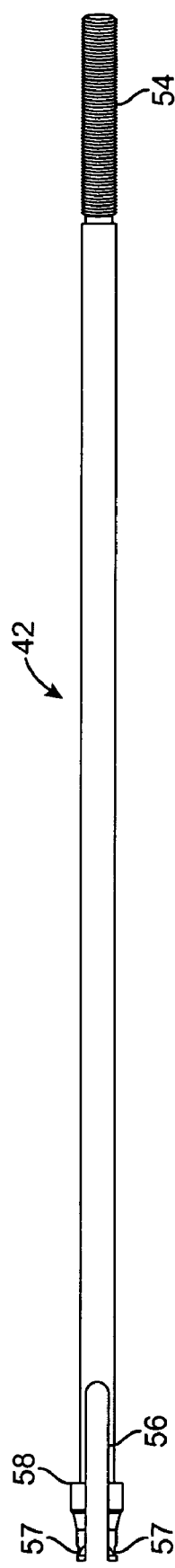
FIG. 4c illustrates a side view of an inner shaft of the shaft assembly of the inserter according to the present invention.

Turning now to FIG. 4c, there is shown a side view of the inner shaft 42. The inner shaft 42 includes a threaded proximal end 54 and a slot 56 at the distal end. The slot 56 opens at the distal end and extends at least partially towards the proximal end of the inner shaft 42. The distal end also includes a shoulder 58 and two aligned bores 57 formed to receive the jaw pin 22.

Figure 4D:
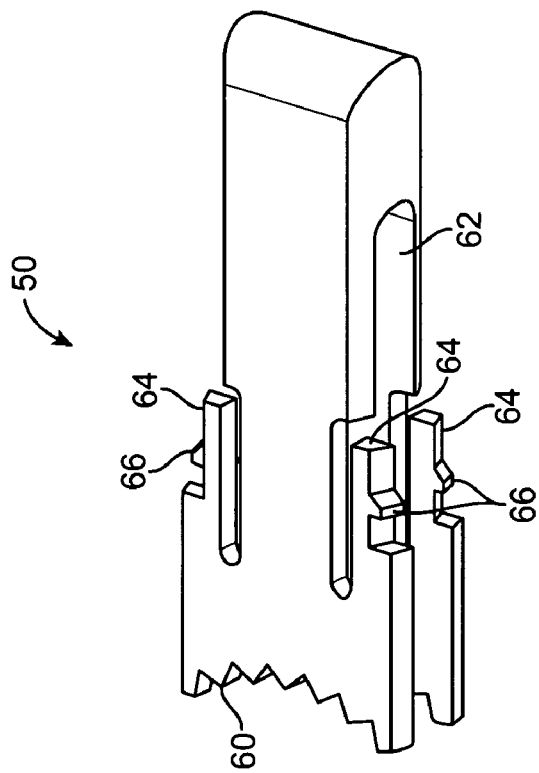
FIG. 4d illustrates a perspective view of an angulation lock according to the present invention.
Figure 4F:
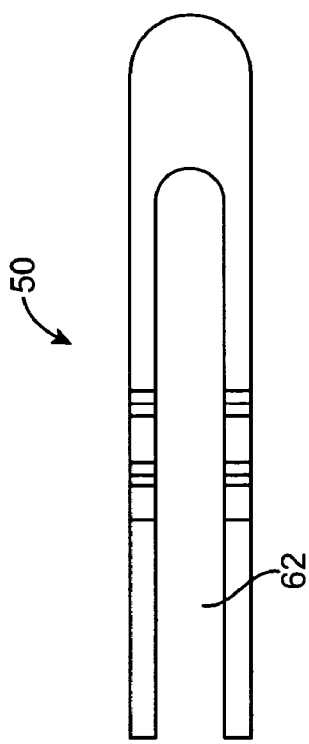
FIG. 4f illustrates a side view of the angulation lock according to the present invention.
Figure 4E:
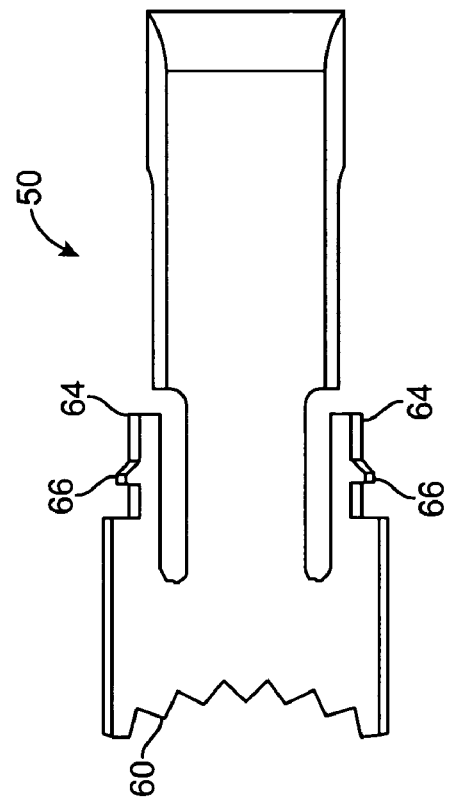
FIG. 4e illustrates a top view of the angulation lock according to the present invention.

Turning now to FIGS. 4d, 4e, and 4f, there are shown perspective, top planar, and side views, respectively, of the angulation lock 50 according to the present invention. The distal end of the angulation lock 50 includes a plurality of teeth 60 and a slot 62 opening at and extending from the distal end towards the proximal end of the angulation lock 50. The slot 62 is configured to receive the pusher 48. The angulation lock 50 further includes four prongs 64. A pair of prongs 64 is located at the top side of the angulation lock 50 and a pair of prongs 64 is located at the bottom side of the angulation lock 50. Each prong 64 extends from the distal end of the angulation lock 50 towards the proximal end of the angulation lock 50 such that the proximal end of each prong 64 is permitted to deflect inwardly. Upon inward deflection, the prongs 64 are configured such that they have the tendency to spring back. Also each prong 64 includes a barb 66.

Figure 4G:
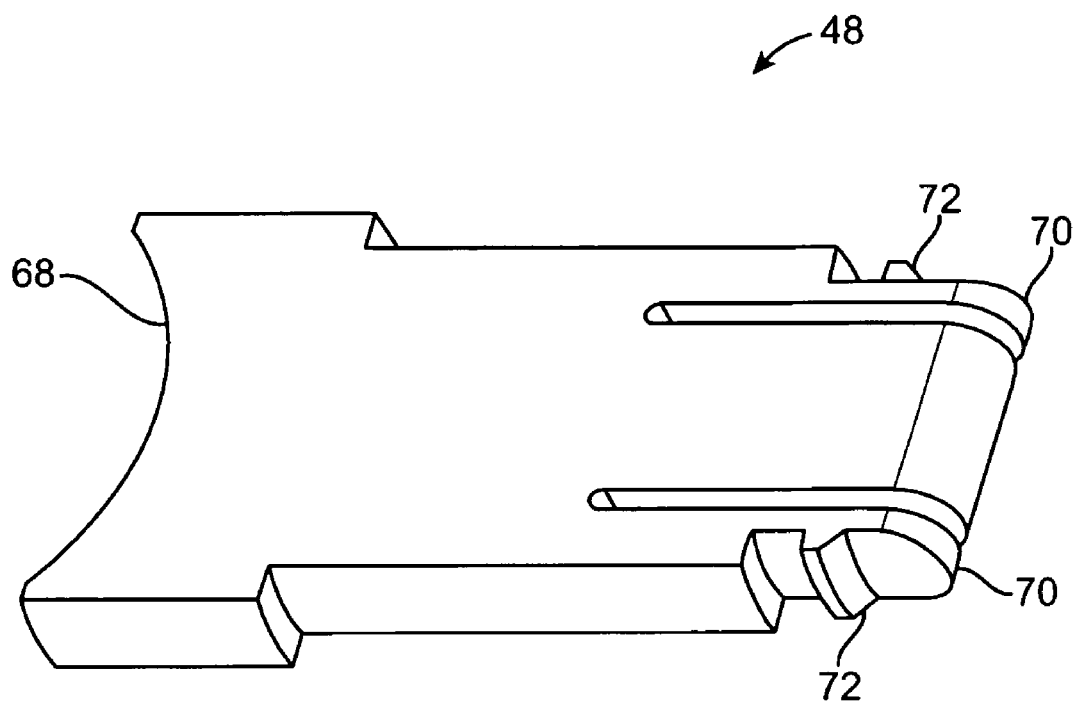
FIG. 4g illustrates a perspective view of a pusher according to the present invention.

Turning now to FIG. 4g, there is shown a pusher 48 according to the present invention. The pusher 48 includes a jaw link engaging portion 68 at the distal end of the pusher 48. The jaw link engaging portion 68 is configured to engage the jaw link 20 of the jaw assembly 12. The jaw link engaging portion 68 includes a surface that conforms to the pusher engaging surface 40 of the jaw link 20. The pusher 48 further includes two prongs 70 that extend from the distal end towards the proximal end of the pusher. The prongs 70 are capable of inward deflection primarily at the proximal end of the prongs 70. Each prong 70 also includes a barb 72 that protrudes outwardly from the prong 70. Upon inward deflection, the prongs 70 are configured such that they have the tendency to spring back.

Figure 4H:
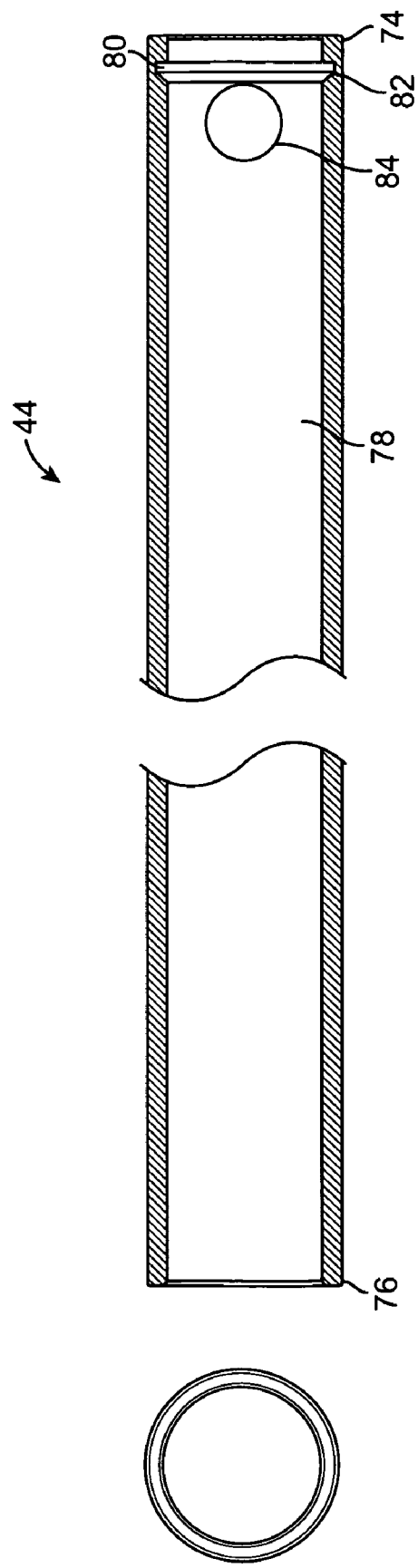
FIG. 4h illustrates a cross-sectional view of a middle shaft according to the present invention.

Turning now to FIG. 4h, there is shown the middle shaft 44 according to the present invention. The middle shaft 44 includes a distal end 74 and a proximal end 76. The middle shaft 44 is configured as a tube having a central bore 78 opening at and extending between the proximal and distal ends, 76, 74. A circumferential inner groove 80 is formed in the inner surface of the bore 78 closer to the distal end 74. The groove 80 is configured to engage the barbs 72 of the pusher 48 and as such, the groove 80 includes an angled surface 82 that corresponds to the angled surface of the barbs 72. At least one window 84 is formed in the middle shaft 44. The window 84 serves as an access point for releasing the barbs 72 from the inner shaft 44 via deflection of the prongs 70.

Figure 4I:
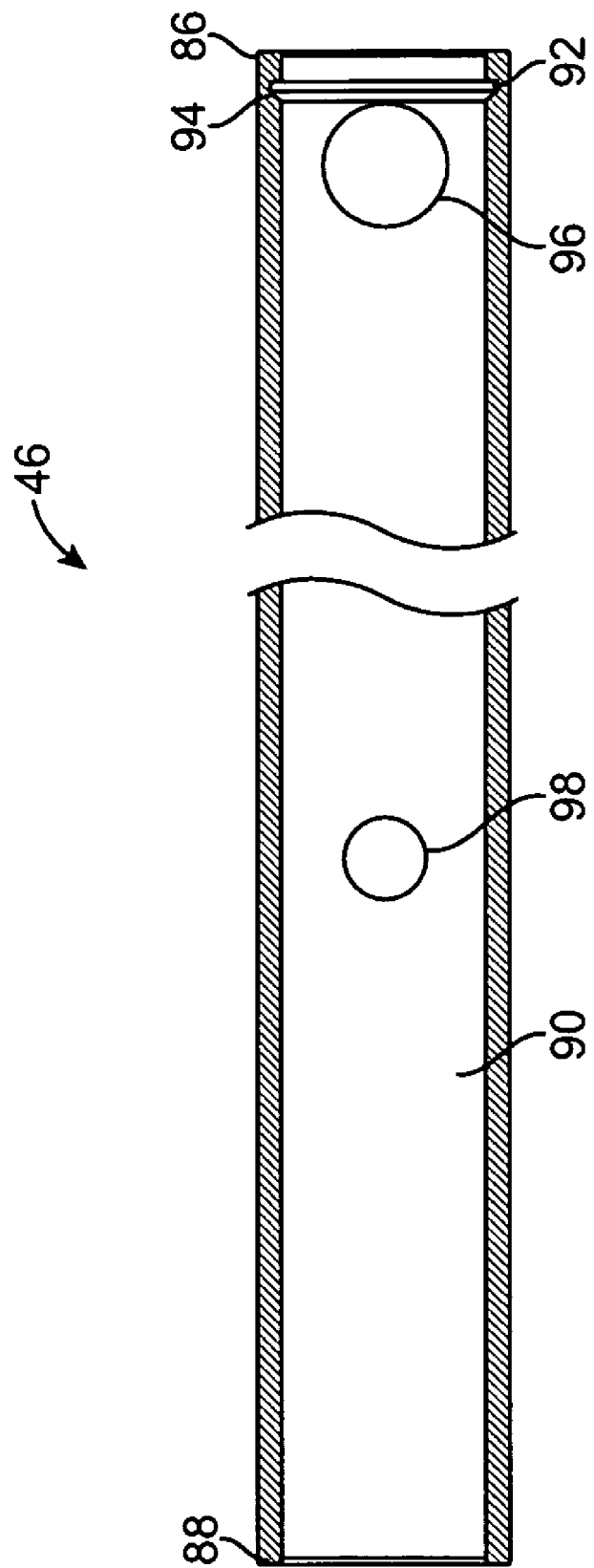
FIG. 4i illustrates a cross-sectional view of an outer shaft according to the present invention.

Turning now to FIG. 4i, there is shown the outer shaft 46 according to the present invention. The outer shaft 46 includes a distal end 86 and a proximal end 88. The outer shaft 46 is configured as a tube having a central bore 90 opening at and extending between the distal and proximal ends, 86, 88. A circumferential inner groove 92 is formed in the inner surface of the bore 90 closer to the distal end 86. The groove 92 is configured to engage the barbs 66 of the angulation lock 50 and as such, the groove 92 includes an angled surface 94 that corresponds to the angled surface of the barbs 66. At least one window 96 is formed in the outer shaft 46. The window 96 serves as an access point for releasing the barbs 66 from the outer shaft 46 via deflection of the prongs 64. Another window 98 is formed closer to the proximal end 88 and is configured for connection to a portion of the hand assembly 16.

The assembly of the shaft assembly 14 will now be discussed. The angulation lock 50 is inserted into the slot 56 of the inner shaft 42 and the pusher 48 is inserted into the slot 62 of the angulation lock 50. The distal end 74 of the middle shaft 44 is passed over the inner shaft 42 from the proximal end of the inner shaft 42. As it passes over the inner shaft 42, the middle shaft 44 engages the pusher 48 and deflects the prongs 70 of the pusher 48 until the barbs 72 of the prongs 70 spring into the groove 80 locking the pusher 48 to the middle shaft 44. The pusher 48 is releasable from the middle shaft 44 by deflecting the prongs 70 inwardly via the window 84 and pulling the pusher 48 free of the middle shaft 44. The distal end 86 of the outer shaft 46 is passed over the middle shaft 44 beginning at the proximal end 76 of the middle shaft 44. As it passes over the middle shaft 44, the outer shaft 46 engages the angulation lock 50 and deflects the prongs 64 of the angulation lock 50 until the barbs 66 of the prongs 64 spring into the groove 92 locking the angulation lock 50 to the outer shaft 46. The angulation lock 50 is releasable from the outer shaft 46 by deflecting the prongs 64 inwardly via the window 96 and pulling the angulation lock 50 free of the outer shaft 46. The spring 52 is passed over the proximal end of the inner shaft 42 until it slides up against the proximal end 88 of the outer shaft 46 which is shorter in length than the middle shaft 44 which is shorter than the inner shaft 42.

Referring back to FIG. 2, the handle assembly 16 includes a knob 100, a handle 102 and fasteners 104. The knob 100 includes finger engaging portions 106 and a bore 108 opening at and extending between the proximal end 110 and the distal end 112. The bore 108 is configured to receive the outer shaft 46 therein.

Figure 5:
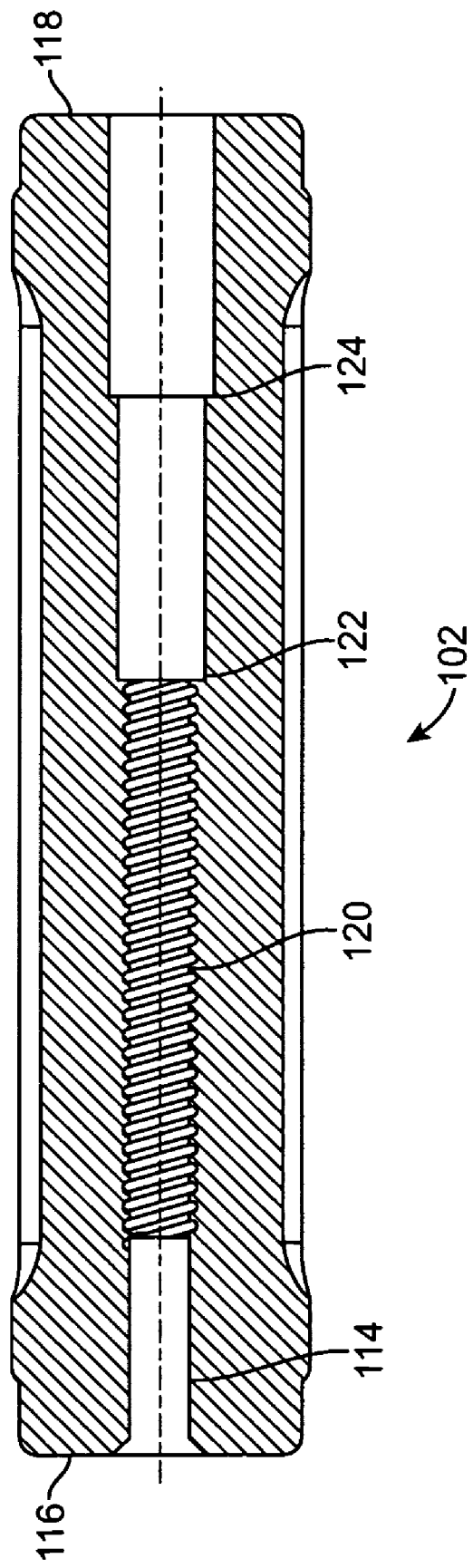
FIG. 5 illustrates a cross-sectional view of a handle according to the present invention.

Turning now to FIG. 5, there is shown a cross-sectional view of the handle 102 having a proximal end 116 and a distal end 118. The handle 102 includes a central bore 114 opening at and extending between the proximal end 116 and the distal end 118. The bore 114 includes a threaded portion 120, a middle shaft ledge 122, and a spring ledge 124.

The assembly of the jaw, shaft and handle assemblies 12, 14, 16 of the instrument 10 will now be discussed. The jaw assembly 12 is inserted into the slot 56 of the inner shaft 42 such that the jaw pin receiving portion 28 is aligned with bores 57 of the inner shaft 42. The jaw pin 22 of the jaw assembly 12 is then passed through the bores 57 and the jaw pin receiving portion 28 in a press-fit engagement thereby connecting the jaw assembly 12 to the shaft assembly 14 such that the jaw assembly 12 is capable of movement with respect to the shaft assembly 14 about the jaw pin 22. The knob 100 of the handle assembly 16 is passed over the proximal end of the inner shaft 42, middles shaft 44 and outer shaft 46 until it is aligned with windows 98 of the outer shaft 46. Fasteners 104 are passed into the knob 100 and into windows 98, connecting the knob 100 to the outer shaft 46. The distal end 118 of the handle 102 is passed over the proximal end of the inner shaft 42 such that the inner shaft 42 is inserted into the bore 114 of the handle 102 until the threaded proximal end 54 of the inner shaft 42 engages the threaded portion 120 of the handle 102. The inner shaft 42 is threaded to the handle 102. Threaded advancement of the shaft assembly 14 inside the bore 114 is arrested by the middle shaft ledge 122 which contacts the proximal end 76 of the middle shaft 44. The spring 52 is disposed and is compressible between the spring ledge 124 and the proximal end 88 of the outer shaft 46.

Figure 6A:
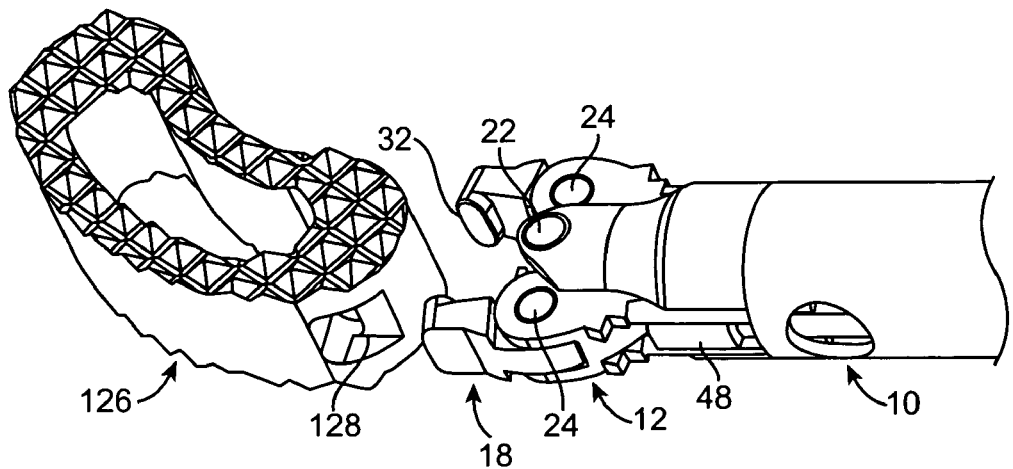
FIG. 6a illustrates a perspective view of a spacer in juxtaposition with the inserter according to the present invention.
Figure 6B:
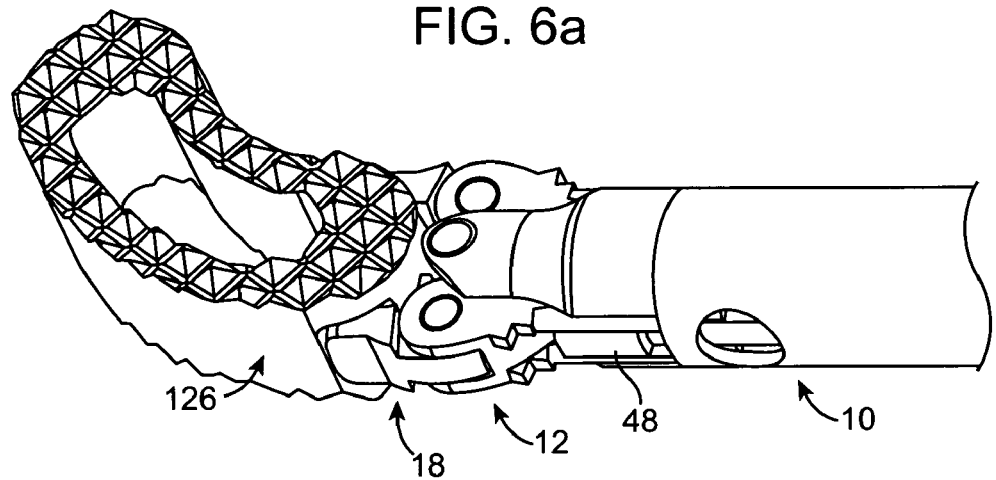
FIG. 6b illustrates a perspective view of a spacer connected to the inserter according to the present invention.
Figure 6C:
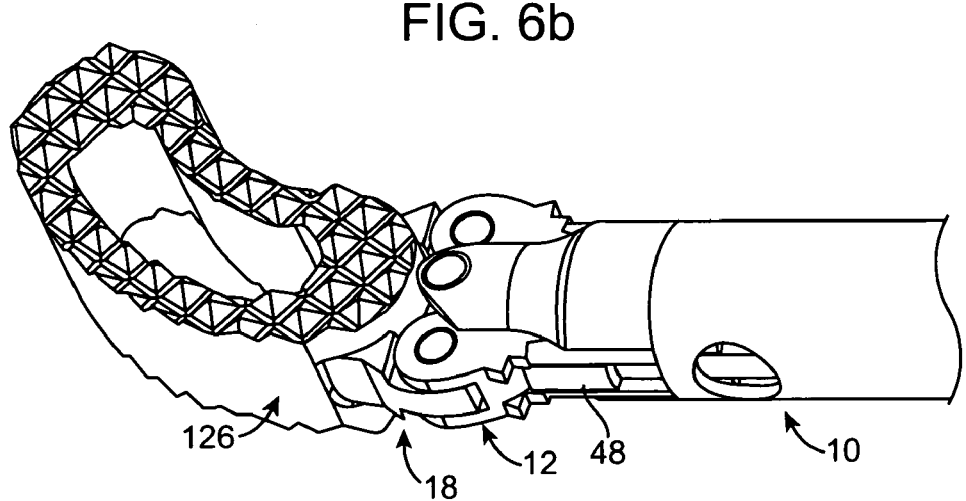
FIG. 6c illustrates a perspective view of a spacer connected to the inserter with the pusher advanced according to the present invention.

Operation of the inserter instrument 10 will now be discussed with initial reference to FIGS. 6a, 6b and 6c. Referring firstly to FIG. 6a, an interbody spacer 126 having engaging apertures 128 is shown in juxtaposition with the inserter 10 with the jaw assembly 12 in an open position in which the jaws 18 are spread apart. The typical spacer 126 includes a body formed by a wall extending about a central cavity. The cavity extends between and opens at an upper bearing surface and a lower bearing surface. The upper and lower bearing surfaces contact the adjacent vertebral endplates to support the adjacent vertebrae when the spacer is implanted into the spinal disc space. Surfaces include grooves formed to facilitate engagement with the vertebral endplates and resist the spacer from migrating within the disc space. The spacer includes a convexly curved anterior wall and an opposite concavely curved posterior wall. These wall portions are connected by a convexly curved leading end wall and a convexly curved trailing end. The overall shape provides a banana or kidney type shape for the spacer.

The spacer 126 includes spacer engaging apertures 128 that are shown in FIG. 6a to be aligned with the spacer engaging features 32 of the jaw assembly 12. The handle 102 is rotated such that the threaded engagement with the inner shaft 42 draws the inner shaft 42 into the bore 114 of the handle 102 and moves the jaw pin 22 along with it, thereby angulating the jaws 18 about pins 22, 24 into a closed position. In the closed position, the spacer engaging features 32 are clamped to the spacer 126 as shown in FIG. 6b. Rotating, or screwing of the handle 102 brings the middle shaft 44 against the middle shaft ledge 122 inside the bore 114 of the handle 102. With the middle shaft 44 abutted against the middle shaft ledge 122, continued advancement, screwing of the handle 102, pushes the middle shaft 44 forward relative to the handle 102 and since the middle shaft 44 is attached to the pusher 48, the pusher 48 moves forward (distally) and contacts the pusher engaging surface 40 of the jaw link 20 biasing it against the jaw 18 to further lock the spacer 126 to the instrument 10 as shown in FIG. 6c. Such advancement also biases the spring 52 between the inside spring ledge 124 and the proximal end 88 of the outer shaft 46. The spring bias pushes the outer shaft 46 forward and because the outer shaft 46 is connected to the angulation lock 50, the teeth 60 of the angulation lock 50 engage the teeth 38 of the jaw link 20 which prevents rotation of the jaw assembly 12 relative to the rest of the instrument 10.

Figure 6D:
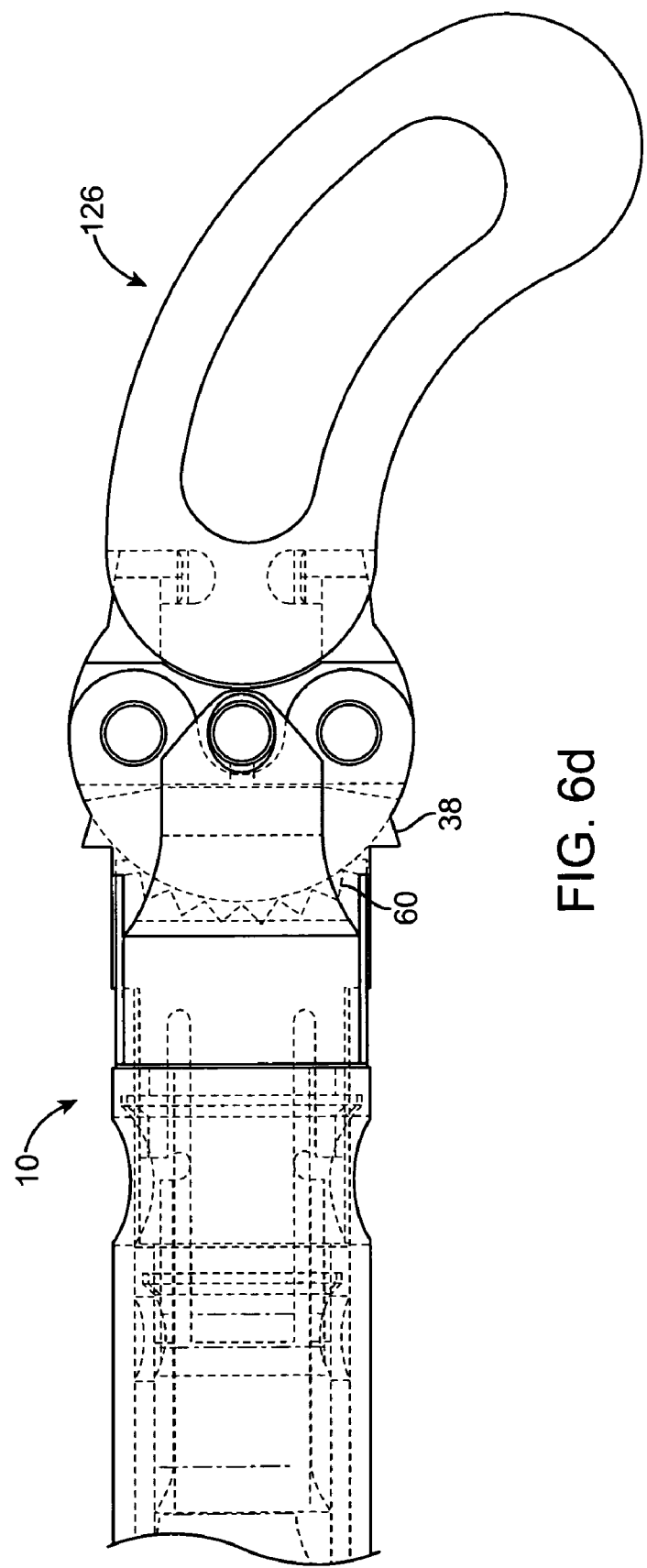
FIG. 6d illustrates a top view of the spacer connected to the inserter in a first orientation according to the present invention.
Figure 6E:
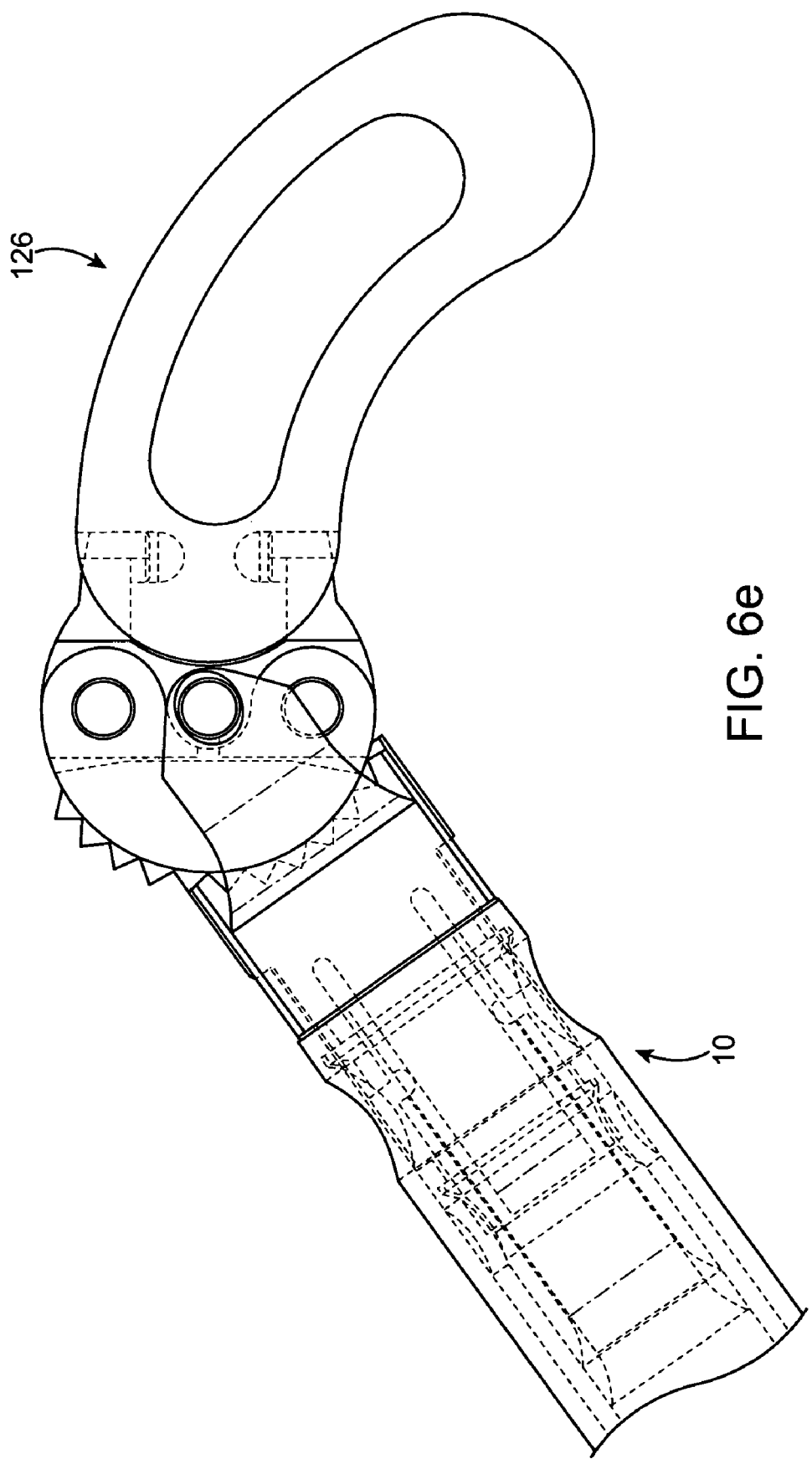
FIG. 6e illustrates a top view of the spacer connected to the inserter in a second orientation according to the present invention.

Pulling on the knob 100 compresses the spring 52 and because the knob 100 is connected to the outer shaft 46 which in turn is connected to the angulation lock 50, the angulation lock 50 is thereby disengaged from the jaw assembly 12, in particular, the teeth 60 of the angulation lock 50 are disengaged from the teeth 38 of the jaw link 20 and the jaw assembly 12 is free to rotate about the jaw pin 22. With the angulation lock 50 thereby disengaged from the jaw link 20, the surgeon is able to angulate the spacer 126 relative to the instrument from, for example, a first orientation such as that shown in FIG. 6d to a second orientation such as that shown in FIG. 6e. Such angulation makes the instrument 10 useful for easing and facilitating insertion, positioning and implantation of the spacer 126 inside the patient. When the knob 100 is released, the spring 52 forces the knob 100 and outer shaft 46 together with the angulation lock 50 forward distally and the teeth 60 of the angulation lock 50 re-engage the teeth of the jaw link 20 thereby locking the two from relative motion. The angulation lock 50 may be repeatedly disengaged and re-engaged as needed by the surgeon to conveniently orientate the spacer advantageously without losing hold of the intervertebral spacer.

The preceding merely illustrates the principles of the invention. Although the description is with respect to the implantation of an intervertebral body spacer, the invention is readily adapted for any spinal implant, including but not limited to spinal implants such as interspinous process spacers, intervertebral body spacers, rods, screws, bone anchors and connectors. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. An inserter for implanting a spinal implant, comprising:
a jaw assembly configured to connect to the spinal implant;
the jaw assembly including:
a jaw having a first jaw piece and a second jaw piece;
a jaw link connected to the first and second jaw pieces such that the first and second jaw pieces are movable with respect to the jaw link;
a shaft assembly connected to the jaw assembly; the shaft assembly including:
an inner shaft connected to the jaw assembly;
an outer shaft having a central bore and located over the inner shaft;
a middle shaft having a bore; the middle shaft being located over the inner shaft and inside the outer shaft; and
an angulation lock connected to a distal end of outer shaft; and
a handle assembly connected to the shaft assembly; the handle assembly including:
a handle connected to the inner shaft; the handle being operable to close and open the jaw to attach and release the spinal implant to and from the jaw; and
a knob connected to the outer shaft and movable with respect to the handle to engage and disengage the angulation lock to and from the jaw assembly so as to disable and enable angulation of the jaw assembly and attached spinal implant with respect to the shaft assembly; and
a pusher configured to engage the jaw link and connected to a distal end of the middle shaft; wherein the inserter is configured such that distal motion of the pusher by action of the handle engages the pusher to the jaw link to lock the jaw link relative to the shaft assembly.

2. The inserter of claim 1, wherein the handle is operable to close and open the jaw by moving the inner shaft proximally and distally with respect to the jaw.

3. The inserter of claim 1, wherein the jaw assembly includes spinal implant engaging features at a distal end.

4. The inserter of claim 1, wherein the inserter is configured to implant a spinal implant selected from the group consisting of an interspinous process spacer, an intervertebral body spacer, a rod, a screw, a bone anchor, and a connector.

5. The inserter of claim 1, wherein the inserter is operable to lock and unlock the attached spinal implant to permit angulation without disconnecting the inserter from the spinal implant.

6. The inserter of claim 1, wherein the jaw link includes angulation lock engaging features and the angulation lock includes jaw link engaging features and the inserter is configured such that distal motion of the outer shaft relative to the jaw link engages the jaw link engaging features of the angulation lock to the angulation lock engaging features of the jaw link to lock the angulation of the jaw assembly relative to the shaft assembly.

7. The inserter of claim 6, wherein the inserter is configured such that proximal motion of the outer shaft relative to the jaw link disengages the jaw link engaging features of the angulation lock from the angulation lock engaging features of the jaw link to unlock the angulation of the jaw assembly relative to the shaft assembly.

8. The inserter of claim 6, wherein the angulation lock engaging features are teeth and the jaw link engaging features are complementary teeth.

9. An inserter for implanting a spinal implant, comprising:
a jaw assembly configured to connect to the spinal implant;
the jaw assembly including:
a jaw having a first jaw piece and a second jaw piece;
a jaw link connected to the first and second jaw pieces such that the first and second jaw pieces are movable with respect to the jaw link;
a shaft assembly connected to the jaw assembly; the shaft assembly including:
an inner shaft connected to the jaw assembly;
an outer shaft having a central bore and located over the inner shaft; and
an angulation lock connected to a distal end of outer shaft; and
a handle assembly connected to the shaft assembly; the handle assembly including:
a handle connected to the inner shaft; the handle being operable to close and open the jaw to attach and release the spinal implant to and from the jaw;
a knob connected to the outer shaft and movable with respect to the handle to engage and disengage the angulation lock to and from the jaw assembly so as to disable and enable angulation of the jaw assembly and attached spinal implant with respect to the shaft assembly;
wherein the jaw link includes angulation lock engaging features and the angulation lock includes jaw link engaging features and the inserter is configured such that distal motion of the outer shaft relative to the jaw link engages the jaw link engaging features of the angulation lock to the angulation lock engaging features of the jaw link to lock the angulation of the jaw assembly relative to the shaft assembly.

10. The inserter of claim 9, wherein the handle is operable to close and open the jaw by moving the inner shaft proximally and distally with respect to the jaw.

11. The inserter of claim 9, wherein the jaw assembly includes spinal implant engaging features at a distal end.

12. The inserter of claim 9, wherein the inserter is configured to implant a spinal implant selected from the group consisting of an interspinous process spacer, an intervertebral body spacer, a rod, a screw, a bone anchor, and a connector.

13. The inserter of claim 9, wherein the inserter is operable to lock and unlock the attached spinal implant to permit angulation without disconnecting the inserter from the spinal implant.

14. The inserter of claim 9, wherein the angulation lock engaging features are teeth and the jaw link engaging features are complementary teeth.

15. An inserter for implanting a spinal implant, comprising:
a jaw assembly configured to connect to the spinal implant;
the jaw assembly including:
a jaw having a first jaw piece and a second jaw piece;
a jaw link connected to the first and second jaw pieces such that the first and second jaw pieces are movable with respect to the jaw link;
a shaft assembly connected to the jaw assembly; the shaft assembly including:
an inner shaft connected to the jaw assembly;

an outer shaft having a central bore and located over the inner shaft; and an angulation lock connected to a distal end of outer shaft; and a handle assembly connected to the shaft assembly; the handle assembly including:

a handle connected to the inner shaft; the handle being operable to close and open the jaw to attach and release the spinal implant to and from the jaw;

a knob connected to the outer shaft and movable with respect to the handle to engage and disengage the angulation lock to and from the jaw assembly so as to disable and enable angulation of the jaw assembly and attached spinal implant with respect to the shaft assembly;

wherein the jaw link includes angulation lock engaging features and the angulation lock includes jaw link engaging features and the inserter is configured such that distal motion of the outer shaft relative to the jaw link engages the jaw link engaging features of the angulation lock to the angulation lock engaging features of the jaw link to lock the angulation of the jaw assembly relative to the shaft assembly; and wherein the inserter is configured such that proximal motion of the outer shaft relative to the jaw link disengages the jaw link engaging features of the angulation lock from the angulation lock engaging features of the jaw link to unlock the angulation of the jaw assembly relative to the shaft assembly.

16. The inserter of claim 15, wherein the handle is operable to close and open the jaw by moving the inner shaft proximally and distally with respect to the jaw.

17. The inserter of claim 15, wherein the jaw assembly includes spinal implant engaging features at a distal end.

18. The inserter of claim 15, wherein the inserter is configured to implant a spinal implant selected from the group consisting of an interspinous process spacer, an intervertebral body spacer, a rod, a screw, a bone anchor, and a connector.

19. The inserter of claim 15, wherein the inserter is operable to lock and unlock the attached spinal implant to permit angulation without disconnecting the inserter from the spinal implant.

20. The inserter of claim 15, wherein the angulation lock engaging features are teeth and the jaw link engaging features are complementary teeth.

\* \* \* \* \*